US00PP13585P2

(12) United States Plant Patent
Kolster

(10) Patent No.: US PP13,585 P2
(45) Date of Patent: Feb. 18, 2003

(54) ROSE PLANT NAMED 'KOLMAG'

(75) Inventor: Peter R. Kolster, Boskoop (NL)

(73) Assignee: Gebr. Kolster B.V., Boskoop (NL)

( * ) Notice: Subject to any disclaimer, the term of this patent is extended or adjusted under 35 U.S.C. 154(b) by 0 days.

(21) Appl. No.: 10/006,843

(22) Filed: Dec. 5, 2001

(51) Int. Cl.[7] ..... A01H 5/00

(52) U.S. Cl. ..... Plt./107

(58) Field of Search ..... Plt./107, 102, 148

*Primary Examiner*—Bruce R. Campell
*Assistant Examiner*—June Hwu
(74) *Attorney, Agent, or Firm*—C. A. Whealy

(57) ABSTRACT

A new and distinct cultivar of Rose plant named 'Kolmag', characterized by its upright and outwardly spreading plant habit; dark green leaflets; single purple-colored flowers; red-colored fruits; and good postproduction longevity.

2 Drawing Sheets

BOTANICAL CLASSIFICATION/CULTIVAR DESIGNATION

*Rosa hybrida* cultivar Kolmag.

BACKGROUND OF THE INVENTION

The present Invention relates to a new and distinct cultivar of Rose plant, botanically known as *Rosa hybrida*, commercially used as cut stems with fruits or hips, and hereinafter referred to by the name 'Kolmag'.

The new Rose is a product of a planned breeding program conducted by the Inventor in Boskoop, The Netherlands. The objective of the breeding program was to develop cut Rose varieties with attractive fruit coloration.

The new cultivar originated from a cross made by the Inventor in 1995 of two unidentified proprietary seedling selections, not patented. The cultivar Kolmag was discovered and selected by the Inventor in 1997 as a flowering plant within the progeny of the stated cross in a controlled environment in Boskoop, The Netherlands.

Asexual reproduction of the new Rose by terminal cuttings taken at Boskoop, The Netherlands, has shown that the unique features of this new Rose are stable and reproduced true to type in successive generations of asexual reproduction.

SUMMARY OF THE INVENTION

The following traits have been repeatedly observed and are determined to be the unique characteristics of 'Kolmag'. These characteristics in combination distinguish 'Kolmag' as a new and distinct cultivar:

1. Upright and outwardly spreading plant habit.
2. Dark green leaflets.
3. Single purple-colored flowers.
4. Red-colored fruits.
5. Good postproduction longevity.

Plants of the new Rose differ from plants of the parent seedling selections primarily in flower and fruit coloration.

Plants of the new Rose can be compared to plants of the Rose cultivar Sensational Fantasy, not patented. In side-by-side comparisons conducted in Boskoop, The Netherlands, plants of the new Rose differed from plants of the cultivar Sensational Fantasy in the following characteristics:

1. Plants of the new Rose had more thorns than plants of the cultivar Sensational Fantasy.

2. Fruits of plants of the new Rose were more intense red in color than fruits of plants of the cultivar Sensational Fantasy.

3. Plants of the new Rose had larger fruits than plants of the cultivar Sensational Fantasy.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph on the first sheet comprises a side perspective view of a typical plant of 'Kolmag' with developed fruits.

The photographs on the second sheet (top to bottom) are close-up views of a typical upper surface of fully expanded leaves of 'Kolmag', a typical opened flower of 'Kolmag' and a typical fruit of 'Kolmag'.

DETAILED BOTANICAL DESCRIPTION

The new Rose has not been observed under all possible environmental conditions. The phenotype may vary somewhat with variations in environment such as temperature, daylength and light intensity, without, however, any variance in genotype.

The aforementioned photographs, following observations and measurements describe plants grown in Boskoop, The Netherlands, in an outdoor nursery and under commercial production practices. Plants were about three years old. The photographs and description were taken during the summer when outdoor day temperatures ranged from 14 to 27° C. and night temperatures ranged from 7 to 12° C. In the following description, color references are made to The Royal Horticultural Society Colour Chart, 2001 Edition, except where general terms of ordinary dictionary significance are used.

Botanical classification: *Rosa hybrida* cultivar Kolmag.

Parentage:

*Female parent.*—Unidentified proprietary selection of *Rosa hybrida*, not patented.

*Male parent.*—Unidentified proprietary selection of *Rosa hybrida*, not patented.

Propagation:

*Type.*—Terminal cuttings.

*Time to initiate roots.*—About 35 days at 20° C.

*Time to produce a rooted young plant.*—About 90 days at 20° C.

*Root description.*—Freely branching; medium thickness; brown in color.

Plant description:

*Plant form.*—Upright and outwardly spreading perennial shrub; globular.

*Growth habit.*—Vigorous. Freely branching; dense and bushy growth habit.

*Growth rate.*—During the spring in Boskoop, The Netherlands, plants grow about 20 cm per month.

*Plant height.*—About 1.7 m.

*Plant width* (*spread*).—About 1.5 m.

*Lateral branches.*—Quantity per plant: About 18. Length: About 90 cm. Diameter: About 4 mm. Internode length: About 2 cm. Strength: Strong. Texture: Glabrous. Color: 143B. Thorns: Density: Moderate. Shape: Triangular with sharp acuminate apices. Height: About 6 mm. Diameter, at base: About 7 mm. Color: N170D.

*Foliage description.*—Leaves alternate; compound with five to nine leaflets. Quantity per lateral branch: About 30. Leaf length: About 10 cm. Leaf width: About 6 cm. Leaflet length: About 4 cm. Leaflet width: About 1.8 cm. Leaflet shape: Elliptic to narrowly ovate. Leaflet apex: Acute. Leaflet base: Rounded to attenuate. Leaflet margin: Serrate. Leaflet texture, upper and lower surfaces: Glabrous; smooth. Leaflet venation pattern: Pinnate. Leaflet color: Developing leaflets, upper surface: 141A. Developing leaflets, lower surface: 143A. Fully expanded leaflets, upper surface: 139A. Fully expanded leaflets, lower surface: 137C. Venation, upper surface: 139A. Venation, lower surface: 143C. Leaf petiole: Length: About 1.6 cm. Diameter: About 1 mm. Texture, upper and lower surfaces: Smooth, glabrous. Leaf rachis texture: Smooth. Color, upper and lower surfaces: 143C. Stipules: Quantity per leaf: Two. Arrangement: One stipule on either side of the leaf petiole. Shape: Lanceolate. Length: About 1.6 cm. Diameter: Less than 1 cm. Color: Upper surface: 141A. Lower surface: 143A.

Flower description:

*Flower type and habit.*—Purple single flowers arranged in compound corymbs with about 25 flowers and flower buds per corymb. Flowers flat and rotate. Flowers not persistent. Flowers face mostly upright or outward.

*Natural flowering season.*—Summer, typically July and August in Boskoop, The Netherlands; flowering period lasts about nine weeks; flowering continuous during this period.

*Postproduction longevity.*—Cut stems are typically harvested when all flowers have developed fruits. Flowers typically last a few days. Postproduction longevity of cut stems with fruits is more than two weeks.

*Fragrance.*—Faint, typical of Rosa, sweet.

*Inflorescence height.*—About 9 cm.

*Inflorescence diameter.*—About 16 cm.

*Flower buds.*—Height: About 2.7 mm. Diameter: About 0.9 mm. Shape: Narrowly ovoid. Color: 143A.

*Flowers.*—Diameter: About 6 cm. Depth: About 1.5 cm.

*Petals.*—Quantity per flower: Five. Length: About 2.6 cm. Width: About 3.1 cm. Shape: Obcordate. Aspect: Reflexed. Apex: Retuse. Base: Attenuate. Margin: Entire. Texture, upper and lower surfaces: Smooth. Color: Developing and fully expanded petals, upper surface: 73A; color fading to N74C with subsequent development. Developing and fully expanded petals, lower surface: 75B.

*Sepals.*—Quantity per flower: Five. Length: About 2.4 cm. Width: About 6 mm. Shape: Narrowly lanceolate. Aspect: Flat to slightly recurved. Apex: Acute. Base: Broadly cuneate. Margin: Entire. Texture: Upper surface: Smooth. Lower surface: Covered with numerous stalked glands. Glands, about 1 mm in length and dark brown in color. Stalks, pale reddish green in color. Color: Developing sepals, upper surface: 138D. Developing sepals, lower surface: 143A. Fully expanded sepals, upper surface: 138D. Fully expanded sepals, lower surface: 143B.

*Peduncles.*—Length: About 3.5 cm. Diameter: About 3 mm. Orientation: About 20 to 35° from vertical. Strength: Strong. Color: 143B.

*Pedicels.*—Length: About 2.5 cm. Diameter: About 2 mm. Orientation: Erect to about 50° from vertical. Strength: Strong. Color: 143B.

*Reproductive organs.*—Stamens: Quantity per flower: About 100. Anther shape: Reniform, irregular. Anther length: About 1 mm. Anther color: 21B to 21C. Pollen amount: Abundant. Pollen color: 4C. Pistils: Quantity per flower: About 30. Pistil length: About 0.5 mm. Stigma shape: Oval, flattened. Stigma color: 157A. Style length: Less than 0.5 mm; minute. Ovary color: 143A to 143B.

*Fruits.*—Quantity per flower: One. Days to ripening: About 40. Type: Fleshy hip. Shape: Roughly spherical. Length: About 1.9 cm. Diameter: About 2 cm. Texture: Sparse stiff short hairs; about 1.5 mm in length; close to N199A in color. Color: N30A to N30B, overlain with 46A; glossy.

*Seeds.*—Quantity per fruit: About 50. Length: About 4.5 mm. Diameter: About 2 mm. Color: 162A to 164C.

Disease susceptibility: Plants of the new Rose have been observed to not be susceptible to pathogens common to Rose, such as mildew and Black Spot.

Temperature tolerance: Plants of the new Rose have been observed to tolerate temperatures ranging from −30 to 35° C.

It is claimed:

1. A new and distinct cultivar of Rose plant named 'Kolmag', as illustrated and described.

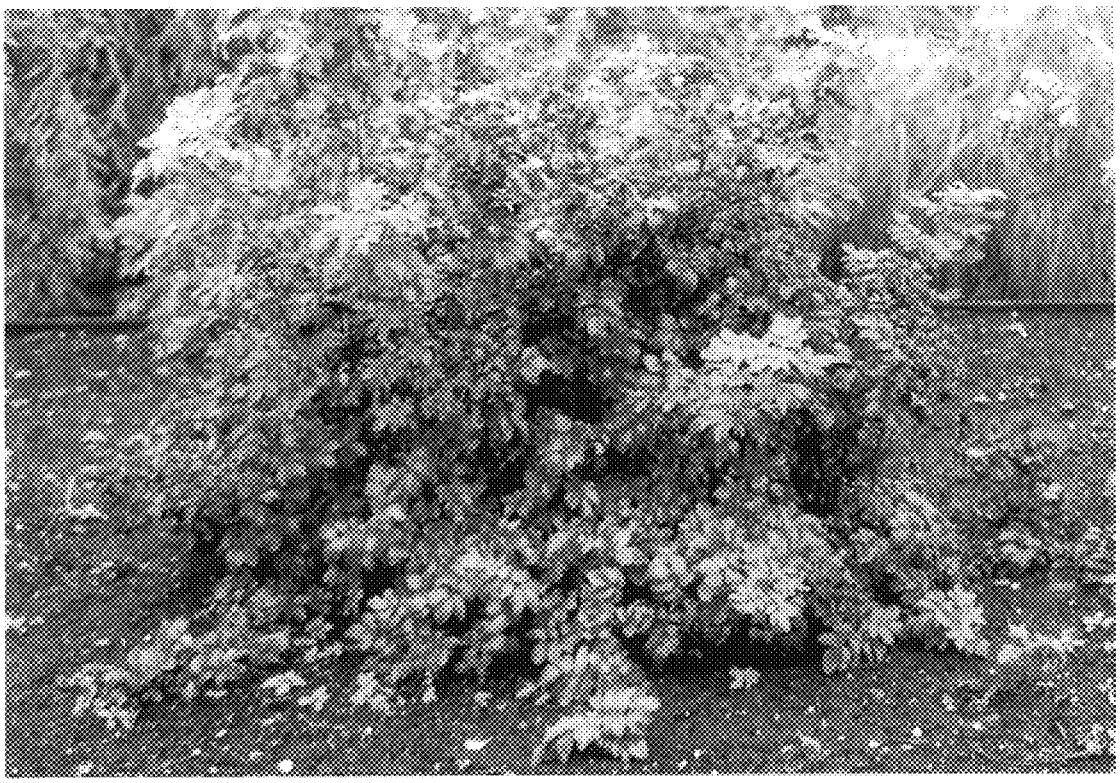

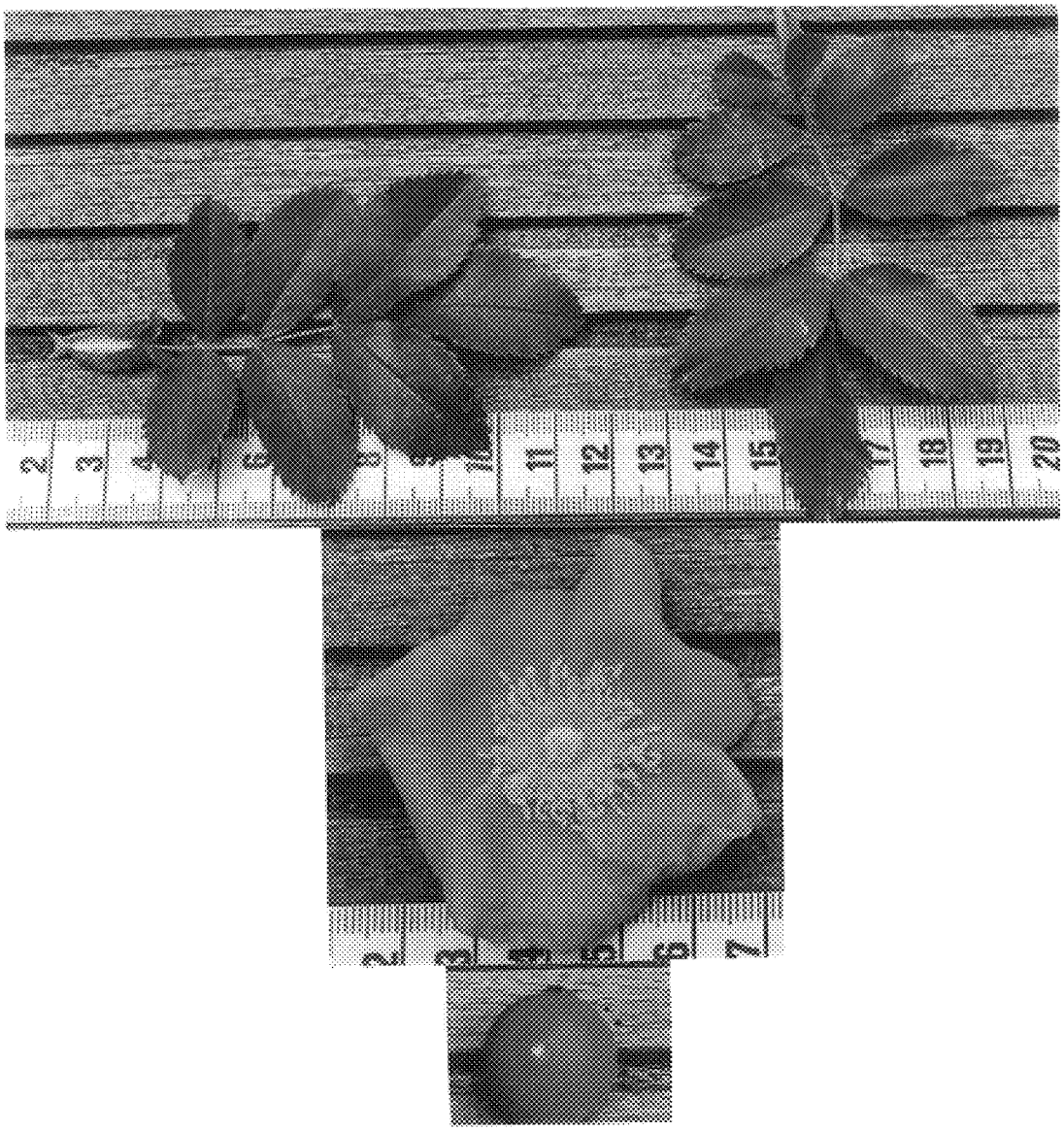

* * * * *